United States Patent [19]

Anderson

[11] Patent Number: 4,986,822
[45] Date of Patent: Jan. 22, 1991

[54] RECTAL-COLON DILATOR AND COLLECTOR ASSEMBLY

[76] Inventor: Irvin B. Anderson, 215 W. College St., Florence, Ala. 35630

[21] Appl. No.: 240,512

[22] Filed: Sep. 6, 1988

[51] Int. Cl.⁵ .......................................... A61M 31/00
[52] U.S. Cl. .................................. 604/276; 604/327; 604/355
[58] Field of Search ............... 128/341, 343; 600/29; 604/275, 276, 287, 288, 327–331, 348, 27, 54, 355; 606/197, 191

[56] References Cited

U.S. PATENT DOCUMENTS

| | | | |
|---|---|---|---|
| 801,924 | 10/1905 | Shiley | 604/39 |
| 2,691,373 | 10/1954 | Bried | 604/275 |
| 3,374,790 | 3/1968 | Mayhorne | 604/347 |
| 3,802,418 | 4/1974 | Clayton | 128/749 |

FOREIGN PATENT DOCUMENTS 0008373 of 1887 United Kingdom ................ 604/278

Primary Examiner—Stephen C. Pellegrino
Assistant Examiner—William Lewis
Attorney, Agent, or Firm—C. A. Phillips

[57] ABSTRACT

A rectal-colon dilator and fecal collector assembly having a tubular member with a meltable cap at one end and an external base member for supporting the tubular member at its other end. The base member has a circular aperture communicating with the tubular member, and a collector bag is connected to communicate with the aperture in sealing relation. A flange around the tubular member near its outer end has screws that engage circular slots in the base member for clamping these parts together by simple rotation of the tubular member with respect to the base member. The base member is saddle-shaped to conform to the patient's body. Upon insertion of the tubular member, peristalsis and defecation are effected in the patient, and fecal matter passes out through the tube and into the collection bag.

3 Claims, 3 Drawing Sheets

RECTAL-COLON DILATOR AND COLLECTOR ASSEMBLY

FIELD OF THE INVENTION

This invention relates generally to devices for stimulating bowel movements and for collecting fecal matter and more particularly to rectal catheter devices.

BACKGROUND OF THE INVENTION

Many patients, particularly the aged and chronically infirm, experience difficulty with bowel movements owing to various medical problems. Some patients lose control over rectal sphincter muscles so that defecation becomes involuntary, and use of a fecal collection device is required. Others have trouble inducing a bowel movement without use of an artificial stimulus or means such as an enema. In these situations, containment of the fecal matter in collecting and handling it has presented a continuing problem. Conventional bed pans put the patient in an uncomfortable position, frequently requiring untenable maneuvers, and often resulting in unsanitary conditions as well as unpleasant odors. Concern for better containment of and sanitation has become heightened recently in handling of patients with Acquired Immune Deficiency Syndrome (AIDS), whose fecal matter may contain infected blood. The need for improved dilator and collector devices arises not only in common situations, but also in intensive care units, surgery, and settings including nursing homes and geriatric care facilities, and whenever non-ambulatory patients require assistance in this regard.

Various devices for collecting fecal matter have been disclosed in prior patents. U.S. Pat. No. 4,182,332 is directed to a rectal catheter having a stool-collecting bag, the neck of which is secured within the patient's rectum by means of an inserted cannula with outwardly biased flanges which hold the neck against the inner wall of the rectum. In U.S. Pat. No. 3,938,521, a fecal collecting bag is connected to and held in place by an inflatable collar inserted in the rectum. This patent also discloses a channel associated with the bag for application of an enema. U.S. Pat. No. 4,496,356 discloses a collector bag secured to an insertable flexible ring and removable by pulling an elongated flexible member. A collector device using an insertable flexible ring communicating with a collector bag is also shown by U.S. Pat. No. 4,030,500. Another approach as disclosed in U.S. Pat. No. 4,067,335 is to use an insertable funnel connected to an unfolding collector tube, the funnel being held in place by ribs connected by webs that exert pressure on the walls of the anal passage or by being inflated upon insertion. These devices all depend on internally disposed means for holding the collector in place, and the inserted support means of such devices are subject to becoming loosened or disengaged, resulting in extreme contamination.

Desirable features for a dilator/collector device include provision of an external means for holding the collector receptacle in place and an insertable dilator for inducing peristalsis and producing a bowel movement, along with a capability for administering medication and for performing enemas. The collector should, of course, provide for maximum sanitation by reliable containment of fecal matter, with minimum exposure of the patient, nurses, or attendants to contamination. Also, the device should be usable as a transporter to a laboratory for examination or for select disposal, with minimized contamination to the environment.

SUMMARY OF THE INVENTION

The present invention is directed to a rectal-colon dilator and fecal matter collector assembly that includes a tubular member for insertion through and into the rectum of a patient, a meltable cap covering the insertable end thereof, a base member or saddle attachable to the patient's body and to the tubular member for supporting the same externally to the patient's body, and a collector bag sealably attached to the other end of the tubular member. This assembly provides both for dilation of the colon, with resulting peristalsis and defecation, and for evacuation of fecal matter through the tubular member into a collector in a manner such as to minimize contamination. Means are also provided for administration of enemas using this assembly. Unlike prior devices, which rely upon inserted rings or other members that apply internal pressure to hold the device in place, the present assembly is held secured in place by an external support member, thus decreasing the possibility of the device becoming loosened and producing severe contamination and/or extreme tenderness, which would result in internal swelling. The present assembly may be employed repeatedly with dependable results and without untoward effects. Use of this assembly will be cost effective owing to fewer bed changes being required, freeing personnel and saving nurses' valuable time. Units embodying the invention may be employed with the patient lying on his or her side, unattended if desired, reducing stress for the patient and nursing staff and expediting patient care procedures. Patient discomfort upon insertion of the capped tubular member would resemble that which would be produced by a heavy bowel movement.

It is, therefore, an object of this invention to provide a rectal-colon dilator and fecal matter collector assembly that may be supported in place on the patient's body by means external to the body.

Another object is to provide such an assembly that includes an insertable member for inducing peristalsis in a patient.

Another object is to provide a fecal matter collector for such assembly that minimizes contamination.

Another object is to provide a rectal-colon dilator and fecal matter collector assembly that enables administration of an enema.

Other objects and advantages of the invention will be apparent from the following detailed description and claims appended hereto.

DESCRIPTION OF THE PREFERRED EMBODIMENT

Figure 1:
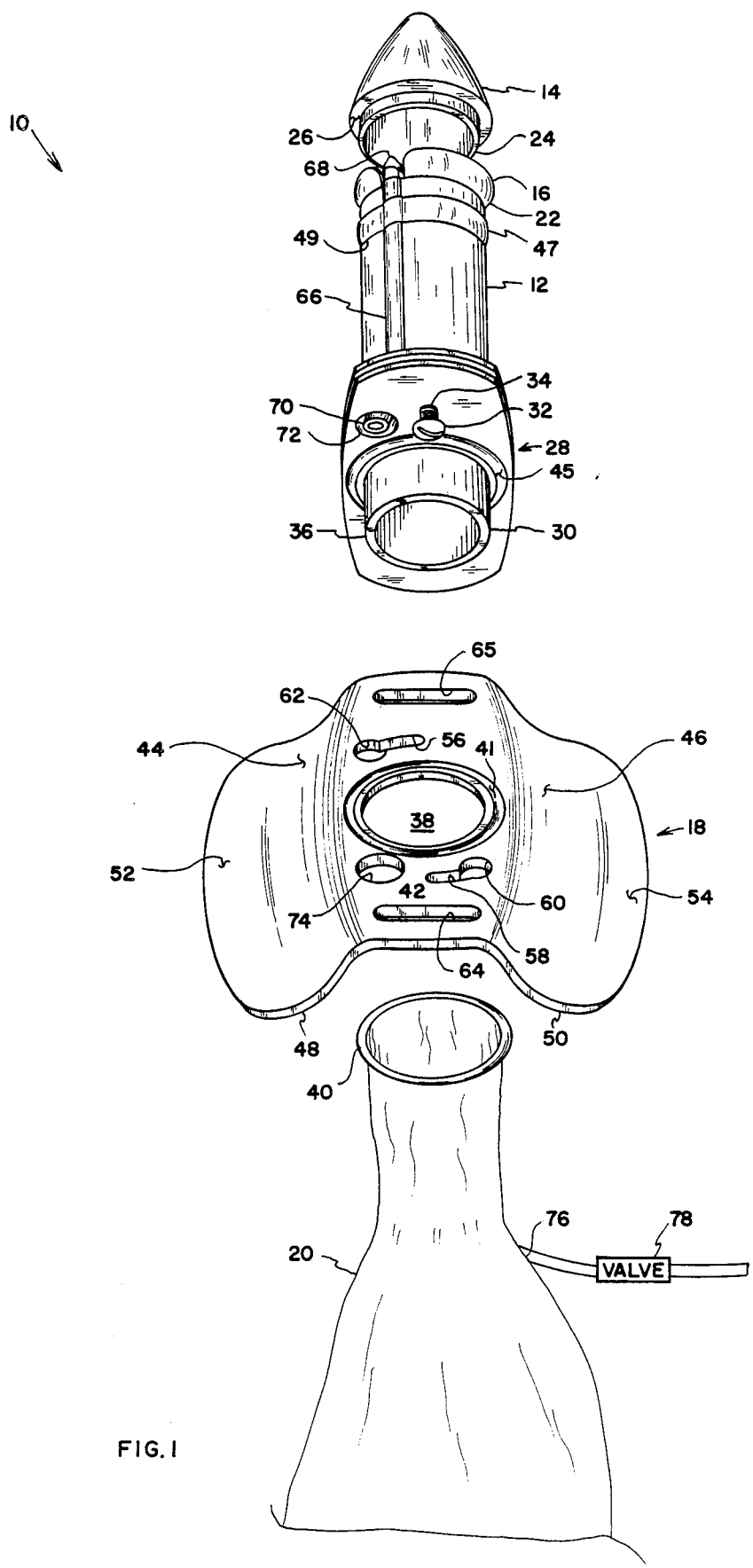
FIG. 1 is an exploded view showing components of applicant's assembly aligned for engagement with one another.

Referring to FIG. 1, a rectal-colon dilator and collector assembly 10 is shown in broken-apart relationship. The device includes an insertable tubular member 12, an end cap 14 for placement on the insertable end 16 of the tubular member, a base member 18 for supporting the tubular member, and a collector bag 20.

The insertable tubular member 12 has a radially flared-out portion 22 adjacent to end 16 for receiving a dome-shaped end cap 14. At its base the end cap has defined therein an annular ring 24 which fits inside flared-out portion 22 and a shoulder 26 which extends over the edge of tubular member 12 at end 16. The radially flared-out portion and mating shoulder, when inserted through the patient's anal ring, dilate the rectum, thus triggering peristalsis and resulting in defecation. End cap 14 is made of a material, such as glycerin, that melts upon exposure to body heat, opening up tube end 16 for passage of fecal matter therethrough. Medication such as aspirin or the like may be incorporated in the end cap material if desired.

Tubular member 12 has a radially extending flange 28 near its outside end 30 for supporting the means used for removably attaching the tubular member to base member 18. In the embodiment shown, screws 32 are axially mounted in threaded holes 34 in a face of flange 28. The flange is spaced apart from end 30 providing an end region 36 for insertion through a central circular aperture 38 in the base member and for providing a passageway or funnel into the bag.

Base member 18 has a saddle-shaped configuration adapted to conform to the patient's body shape. Middle region 42 has a truncated elliptical shape and is flat so as to support tubular member 12 in perpendicular relation thereto with aperture 38 in alignment with the patient's rectum. Side regions 44 and 46, integral with middle region 42, are curved away from the plane of the middle region as shown at 48 and 50 forming generally flat regions 52 and 54 that are spaced apart from the middle region and are engageable with the patient's buttocks when the middle region is disposed in the rectal area. Base member 18 is preferably made of a plastic material having a moderate degree of flexibility so as to allow movement of flat regions 52 and 54 toward and away from middle region 42 and thus to accommodate patients of varying size.

Middle region 42 of base member 18 has extending therethrough slots 56 and 58 disposed circumferentially with respect to aperture 38 and having enlarged circular regions 60, 62 at their clockwise rearward ends, the enlarged regions allowing the heads of screws 32 to pass through the slots and the remaining narrower portions of the slots restraining the screw heads in place upon clockwise circular movement of the screws within the slots. For disengagement of the base member, it may be rotated counterclockwise, aligning the screw heads with the enlarged regions 60, 62 and allowing the screw heads to be moved axially through the enlarged portions. Middle region 42 also has a pair of slots 64 and 65 near its exposed edges and spaced apart therefrom for receiving a belt or strap (not shown) for securing the base member and attached tubular member in position on the patient. The base member may also be secured to the patient's body by taping.

Figure 3:
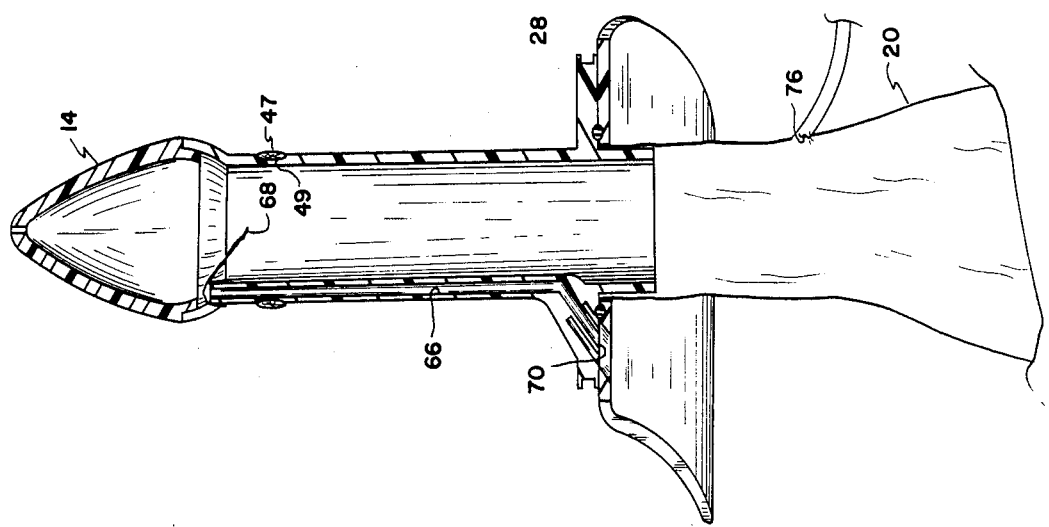
FIG. 3 is a sectional view taken along line 3—3 of FIG. 2.

In order to enable irrigation of the patient's colon for purposes such as an enema, the tubular member has incorporated in its wall an axially extending tubular passageway 66 communicating with a flexible, self-closing tube segment 68 and with external means (not shown) for supplying a liquid. As shown in FIG. 3, the passageway 66 at its juncture with flange 28 extends slightly radially at an angle of 30° and terminates in end 70 disposed within circular opening 72, with its outer wall in sealed relationship to the flange, the 30° curvature being provided to give better access to end 70. End 70, when aligned within circular aperture 74 in middle region 42 of the base member, may be connected to a hose communicating with a liquid supply (not shown) upon engagement of the tubular member with the base member. Tube segment 68 is made of flexible material, normally biased closed, but openable upon application of pressure by a liquid stream. Prior to placement of cap 14 in position on end 16 of the tubular member, segment 68 may be folded over inside the tubular member so as not to interfere with its insertion. Upon melting of the cap and application of liquid pressure, segment 68 opens and is projected axially, allowing the liquid to pass through. Upon cessation of liquid flow, segment 68 returns to its closed position, folded inside the tube. This structure prevents flow of fecal-matter-containing liquid out through passageway 66 after administration of an enema and, owing to its small size and folded over condition, segment 68 does not significantly interfere with flow of liquid and fecal matter outward through tubular member 12.

Collecting bag 20, which may be made of thin rubber material with sufficient strength to support the weight of fecal matter and liquid, may be secured between flange 28 and base member 18 by means of threading the open end thereof through aperture 38 and disposing ring 40, integral with the open end of the bag, in a circumferential groove 41, provided in flat surface 42, surrounding and spaced apart from aperture 38. Upon bringing the flange and base member together, ring 40 is clamped between groove 41 and a mating circumferential surface 45 at the outer end of the flange. Bag 20 is preferably provided with an opening 76 communicating with valve 78 for release of expelled gas and to prevent bag expansion.

In order to provide better control of contamination, a ring 47 of a swellable absorbent, such as cellulosic or tampon-type material, may be disposed near the insertable end of tubular member 12 in a circumferential groove 49 spaced apart slightly from flared out portion 22.

Figure 2:
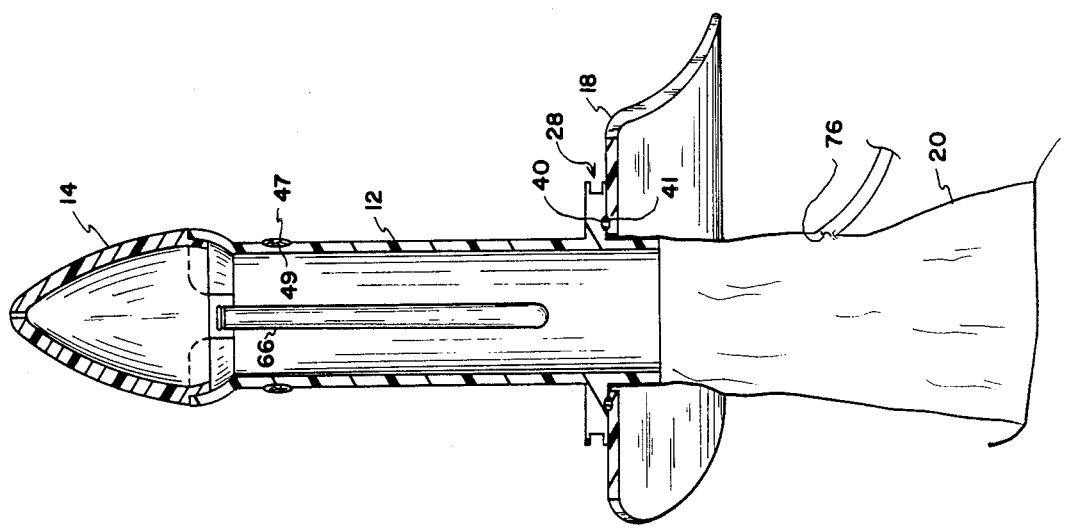
FIG. 2 is a partially cut-away view showing the assembly of FIG. 1 in engaged condition.

FIG. 2 shows the device of FIG. 1 in assembled condition. In this embodiment, the collector bag 20 is secured in sealed relationship with tubular member 12 by virtue of end ring 40 of bag 20 being clamped between flange 28 and base member 18 within groove 41.

FIG. 3 shows tube segment 68 in its normally folded-over closed condition as would exist except when liquid pressure is being applied through tubular passageway 66. The lower portion of passageway 66 is shown extending diagonally through flange 28 and terminating at end 70, which is accessible through aperture 74 for attachment to a supply of liquid so as to enable administration of an enema.

Figure 4:
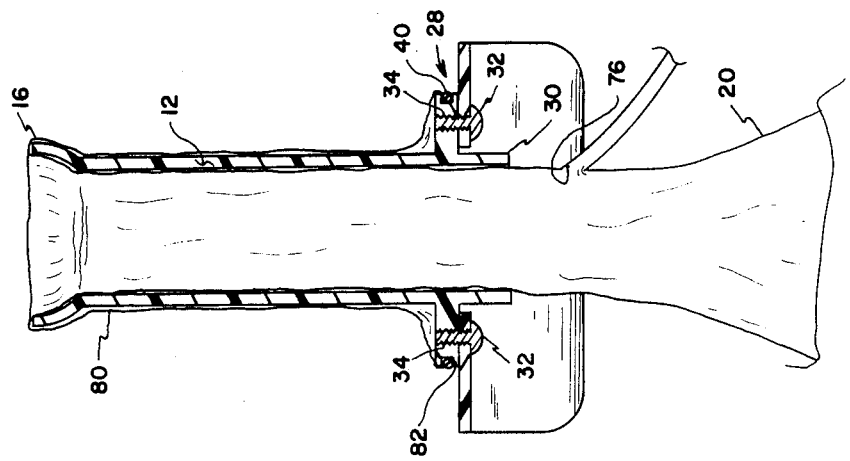
FIG. 4 is a cut-away view, with the cap removed, showing another embodiment of the invention.

FIG. 4 shows an embodiment of the invention wherein tubular member 12 does not include a passageway for conveying a liquid to the cap region. The cap is omitted in this view for purposes of clarity. The swellable ring is omitted, and the collector bag is connected with the tubular member in a different manner. In this embodiment, the collector bag 20 is provided with an elongated neck region 80 so as to enable the end ring 40 of the bag to be secured in a circumferential groove 82 in the outward facing edge of flange 28. The neck of the bag is threaded upward over the outside of the tubular member and downward inside and past end 16 and end 30. The meltable cap fits within the inserted neck of the bag at flared-out portion 22 of the tubular member. This embodiment prevents the outside of the tubular member from becoming contaminated, the exposed, contaminated neck portion of the bag retaining contamination upon being being moved upward and dropping through the tubular member after use. This structure may be used in situations where adminstration of an enema is not required.

Figure 5:
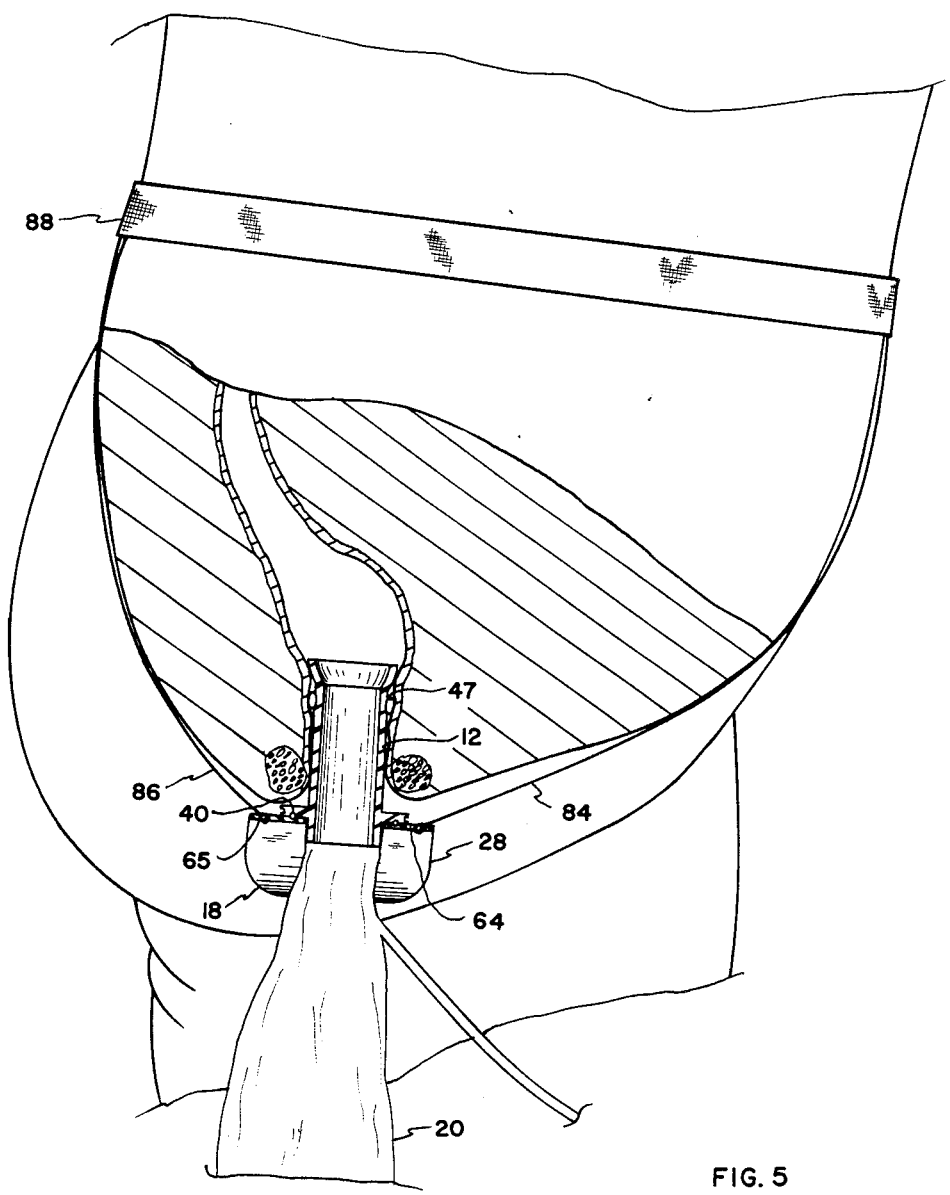
FIG. 5 is a partially cut-away view showing the assembly of FIG. 1 in place and secured to the body of a patient.

FIG. 5 shows an assembly of the present invention inserted for use and secured to the body of a patient. Strap 84 connected to the base member through slot 64 therein and strap 86 connected through slot 64 are secured to a belt 88 encircling the patient's waist. The base member is held firmly against the patient's body by this means, preventing accidental removal. The base member may also be secured to the patient's body by taping.

I claim:

1. A rectal-colon dilator and fecal collector assembly comprising:
   a tubular member for insertion through the rectum and into the colon of a patient and having a radially flared-out insertable end and an outside end;
   a meltable cap closing said insertable end;
   a base member attachable to the outside end of said tubular member for supporting the same externally to the patient's body, said base member being saddle-shaped and having a flat middle portion with a circular aperture adapted to be placed over the patient's rectum and generally perpendicular thereto and side portions spaced apart from and generally parallel to said middle portion and adapted to engage said patient's buttocks;
   a ring of swellable absorbent material disposed on the outside of said tubular member in spaced-apart relation from said flared-out insertable end; and
   a collector bag sealably attached to said tubular member.

2. An assembly as defined in claim 1 including a circumferential groove in the outside of said tubular member for retaining said ring of absorbent material.

3. A rectal-colon dilator and fecal collector assembly comprising:
   a tubular member for insertion through the rectum and into the colon of a patient and having a radially flared-out insertable end and an outside end;
   a meltable cap closing said insertable end;
   a base member attachable to the outside end of said tubular member for supporting the same externally to the patient's body, said base member being saddle-shaped and having a flat middle portion with a circular aperture adapted to be placed over the patient's rectum and generally perpendicular thereto and side portions spaced apart from and generally parallel to said middle portion and adapted to engage said patient's buttocks;
   a flange secured to and disposed perpendicular to said tubular member at a location near, but spaced apart from, said outside end, a middle portion of said base member being engageable by rotation with means projecting perpendicularly from said flange member;
   a collector bag sealably attached to said tubular member;
   a circumferential groove surrounding and spaced apart from said aperture in said base member and on the outside face thereof for receiving an end of said collector bag and retaining the same in sealing relation to said tube when said flange is engaged with said base member;
   strap means attachable to said patient's body and means for connecting said strap means to said base member;
   an aperture in a side of said collector bag and valve means communicating therewith for release of gas;
   a channel associated with the wall of said tubular member for communicating the insertable end thereof with an external liquid source; and
   a flexible, normally closed tip member communicating with said channel and openable upon application of liquid pressure therethrough.

* * * * *